(12) United States Patent
Westmarland et al.

(10) Patent No.: US 9,874,540 B2
(45) Date of Patent: Jan. 23, 2018

(54) SUPPORT FOR ELECTRODE STACK AND PROVISION FOR VENTING OF A GAS SENSOR USING AN INTERNALLY MOUNTED TABLE

(71) Applicant: Life Safety Distribution AG, Hegnau (CH)

(72) Inventors: Paul Christopher Westmarland, Byfleet (GB); Martin Jonathan Kelly, Clanfield (GB); John Chapples, Portsmouth (GB); Neils Richard Stewart Hansen, Poole (GB); Arkadiusz Edward Majczak, Hampshire (GB); Stuart Alistair Harris, Bournemouth (GB)

(73) Assignee: Life Safety Distribution AG, Hegnau (CH)

( * ) Notice: Subject to any disclaimer, the term of this patent is extended or adjusted under 35 U.S.C. 154(b) by 470 days.

(21) Appl. No.: 14/506,312

(22) Filed: Oct. 3, 2014

(65) Prior Publication Data
US 2015/0122649 A1  May 7, 2015

Related U.S. Application Data

(60) Provisional application No. 61/900,669, filed on Nov. 6, 2013.

(51) Int. Cl.
*G01N 27/403* (2006.01)
*G01N 27/404* (2006.01)

(52) U.S. Cl.
CPC ......... *G01N 27/403* (2013.01); *G01N 27/404* (2013.01)

(58) Field of Classification Search
CPC .................................. G01N 27/403–27/4045
USPC ................................ 204/412, 415, 431, 432
See application file for complete search history.

(56) References Cited

U.S. PATENT DOCUMENTS

| 4,042,464 | A | * | 8/1977 | Blurton | G01N 27/4045 204/411 |
|---|---|---|---|---|---|
| 4,477,403 | A | * | 10/1984 | Pust | G01N 27/404 204/421 |
| 5,284,566 | A | * | 2/1994 | Cuomo | G01N 27/4045 204/412 |
| 5,338,429 | A | | 8/1994 | Jolson et al. | |
| 2005/0145493 | A1 | * | 7/2005 | Saffell | G01N 27/4045 204/431 |
| 2006/0032742 | A1 | * | 2/2006 | Babes-Dornea | G01N 27/4045 204/400 |

(Continued)

FOREIGN PATENT DOCUMENTS

| CN | 1113007 A | 12/1995 |
|---|---|---|
| CN | 102597765 A | 7/2012 |

(Continued)

OTHER PUBLICATIONS

Extended European search report from corresponding application EP 14188914.7, dated Mar. 24, 2015.

(Continued)

*Primary Examiner* — Bach T Dinh
(74) *Attorney, Agent, or Firm* — Conley Rose, P.C.

(57) ABSTRACT

A sensor with a sensor housing or body, a plastic molded table positioned in the sensor housing; and a counter electrode carried on a first end of the table.

21 Claims, 10 Drawing Sheets

(56) References Cited

U.S. PATENT DOCUMENTS

2006/0257288 A1* 11/2006 Sun .................... G01N 27/404
422/89

FOREIGN PATENT DOCUMENTS

| EP | 1 600 768 A1 | 11/2005 |
| EP | 2 581 734 A2 | 4/2013 |
| GB | 2 303 710 A | 2/1997 |
| WO | WO 95/22055 A1 | 8/1995 |
| WO | WO 2007/087632 A2 | 8/2007 |
| WO | WO 2011/053721 A1 | 5/2011 |

OTHER PUBLICATIONS

China Patent Application No. 201410614877.X, Office Action, dated Sep. 26, 2016, 14 pages.
Europe Patent Application No. 14188914, Communication Under Rule 71(3) EPC, dated Jun. 28, 2016 29 pages.
Europe Patent Application No. 14188914, Communication Under Rule 71(3) EPC, dated Oct. 18, 2016 29 pages.

* cited by examiner

SUPPORT FOR ELECTRODE STACK AND PROVISION FOR VENTING OF A GAS SENSOR USING AN INTERNALLY MOUNTED TABLE

CROSS-REFERENCE TO RELATED APPLICATION

This application claims the benefit of the filing date of U.S. Provisional Application No. 61/900,669 filed Nov. 6, 2013, entitled "Support for Electrode Sack & Provision for Venting of a Gas Sensor Using an Internally Mounted Table." Application No. 61/900,669 is incorporated herein by reference.

FIELD

The application pertains to electrochemical oxygen sensors. More particularly, the application pertains to such sensors, which have an external housing that supports an internally fitted table that supports an electrode stack assembly. Furthermore, this application relates to the use of Aclar® as a barrier material in electrochemical gas sensors.

BACKGROUND

An oxygen pump sensor requires a vent in order to operate where oxygen gas is consumed at the sensing electrode and generated at the counter electrode. A connection to the exterior atmosphere is therefore required when the counter electrode is placed at the base of the electrode stack in order to vent the generated oxygen from inside the sensor. One method of providing venting to the counter electrode at the base of the stack is to extend a molded tube to meet the electrode (e.g., the City Technology, ECO-OX).

An electrode stack within an oxygen pump sensor also requires adequate physical support to maintain consistent stack compression. The compression of the electrode stack facilitates electrical contact with the current collectors, and ensures adequate transfer of electrolyte to the separators within the stack.

DETAILED DESCRIPTION

Figure 1:
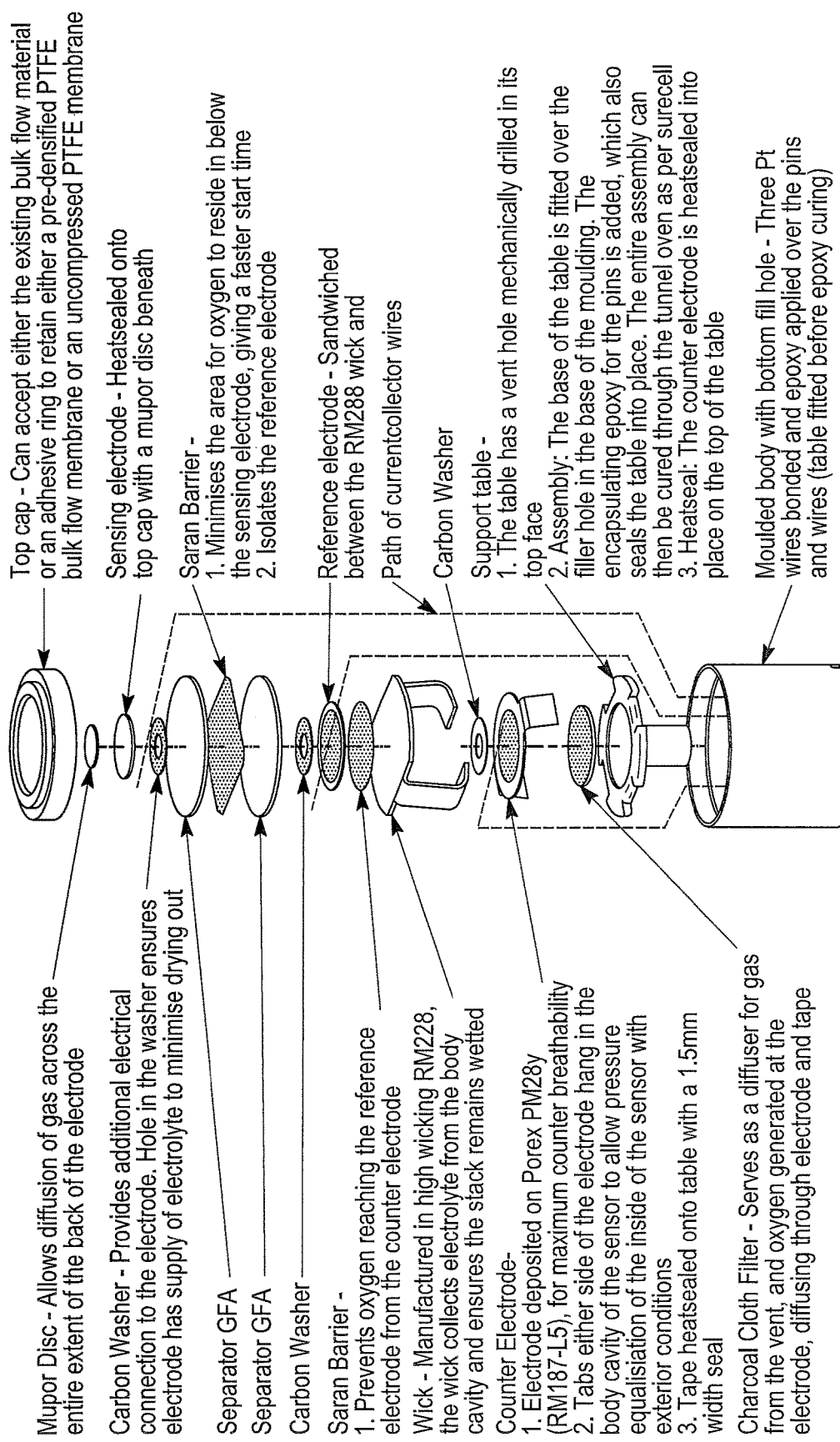
FIG. 1 is an exploded view of a sensor in accordance herewith.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

The subject matter hereof provides a sensor having a two piece molding, comprising an existing main body containing terminal pins, a gas inlet port or hole in the base, and an internally fitted 'table', which supports the electrode stack assembly. The table has a hollow central leg, which is sealed into the sensor body with an epoxy, whose primary purpose is to prevent egress of electrolyte via the inserted terminal pins. Another purpose of the epoxy is to prevent corrosion of the pins, which can generate currents and will eventually make leakage more likely. The epoxy also serves to hold the table legs in place. The table's hollow central leg also supports the electrode stack assembled on top of it. One useful aspect of this design is that the use of PTFE counter tape promotes quick equalization of sensor interior pressure with the atmospheric pressure outside the sensor, greatly reducing the possibility of the sensor 'glitching'. Those of skill will understand how to select the grade of such tape.

The 'table' is an injection molded item. The molded sensor initially has at least one current collector or wires welded to the top of the terminal pins. Epoxy is then dispensed into the base of the sensor body, covering the internal base of the sensor and the top of the terminal pins. The gas inlet port is a protrusion in the center of the base and sits above the height of the epoxy, so that the epoxy does not leak out of the sensor body molding during curing and to ensure that the epoxy does not get into the vent and obscure the hole.

The table is then added to this epoxy before the epoxy has cured. The table sits over the protrusion in the center of the base of the molding, and the epoxy is allowed to cure. The epoxy is exothermic, but curing time is decreased by passing through an oven. This also promotes a drop in viscosity of the epoxy, which ensures that it flows around the table leg and seals it in place.

The lower viscosity also ensures the table settles correctly onto the floor of the sensor body molding, although a tight fitting table to sensor body protrusion also promotes positive, consistent location. In this way, a gas pathway has been created from the exterior base of the sensor body up to the bottom of the electrode stack, which is situated at the top of the sensor body.

In one embodiment, the sensor comprises a body having at least one terminal pin connected to at least one current collector, and a gas inlet port, a table with a gas inlet port in alignment with the gas inlet port of the body, at least one leg seated on the body near the at least one terminal pin, a vent membrane carried on the table, a counter electrode carried on the vent membrane, a reference electrode in communication with but separated from the counter electrode by at least one washer or pad, a sensing electrode in communication with but separated from the reference electrode by at least one washer or pad, and a cap on top of the sensing electrode, in which cap attaches to the body and forms a seal to contain an enclosed electrolyte.

In another embodiment, the sensor comprises a housing, at least two electrodes, an electrolyte, and at least one separator, wherein the at least one separator includes polychlorotrifluoroethylene.

In yet another embodiment, the sensor comprises an electrode stack including at least a sensing electrode and a counter electrode; electrolyte between the electrodes; a table which carries the electrode stack; a housing, which carries the electrolyte and the table, wherein the table provides a venting route connecting a selected region of the stack to an outside surface of the housing.

In still yet another embodiment, the sensor comprises a housing, at least two electrodes, an electrolyte, and a vent membrane in communication with a vent leading to an external atmosphere.

Figure 2A:
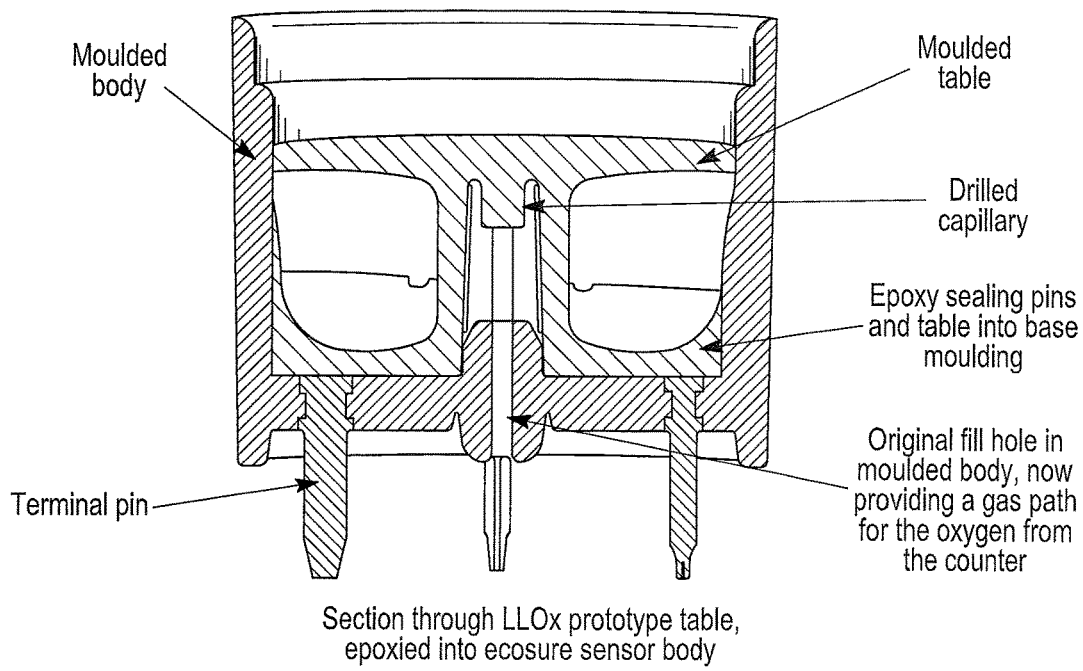
FIG. 2A is an enlarged side view of a support table.
Figure 2B:
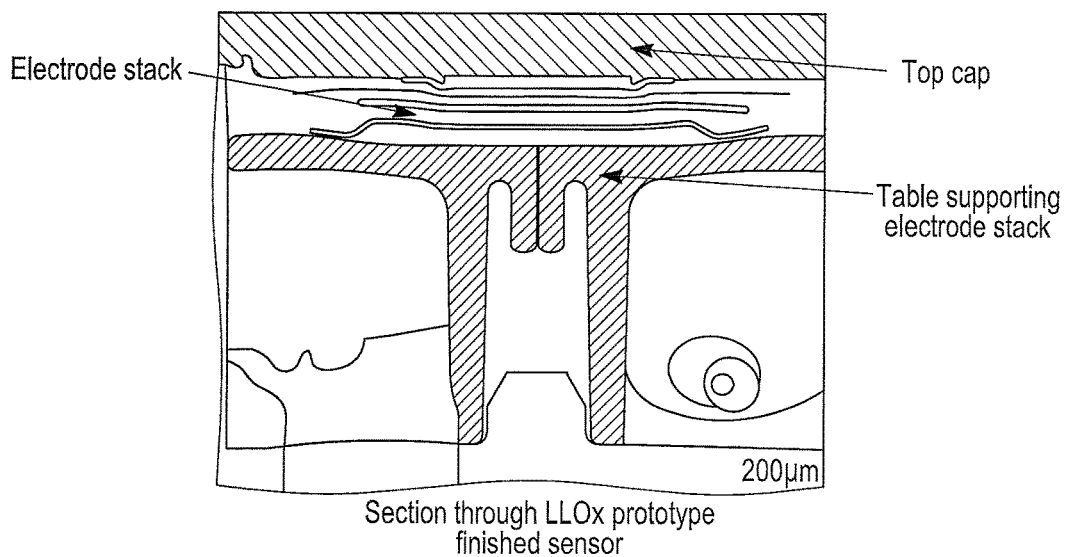
FIG. 2B is an enlarged section illustrating an electrode stack and supporting table.
Figure 3:
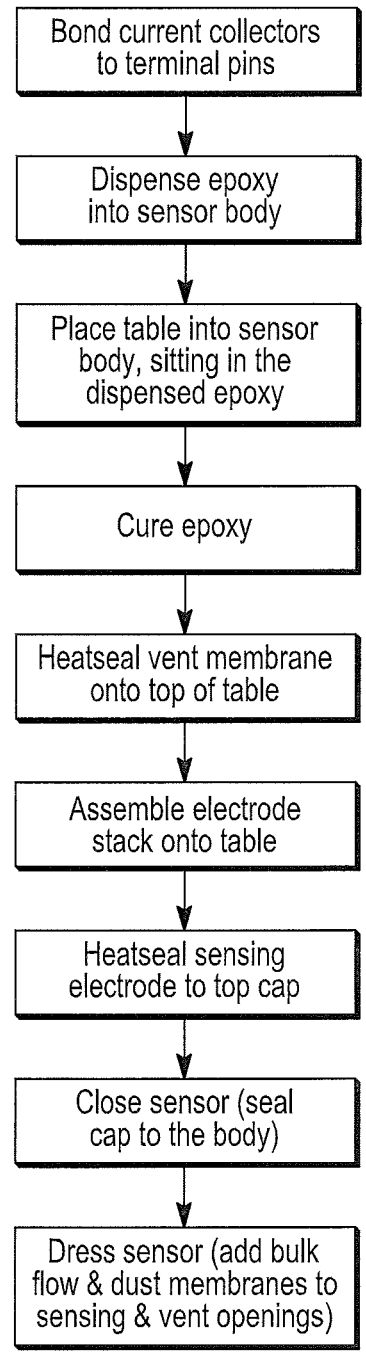
FIG. 3 is an assembly flow chart.
Figure 4A:
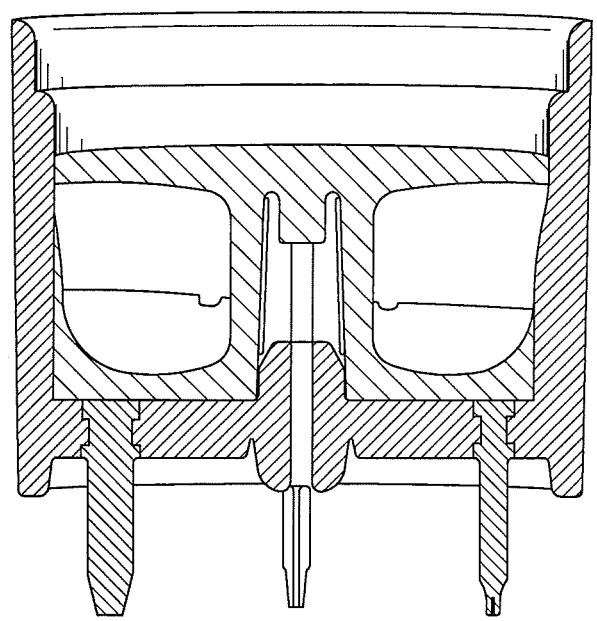
FIG. 4A is an enlarged side sectional view of the supporting table.
Figure 4B:
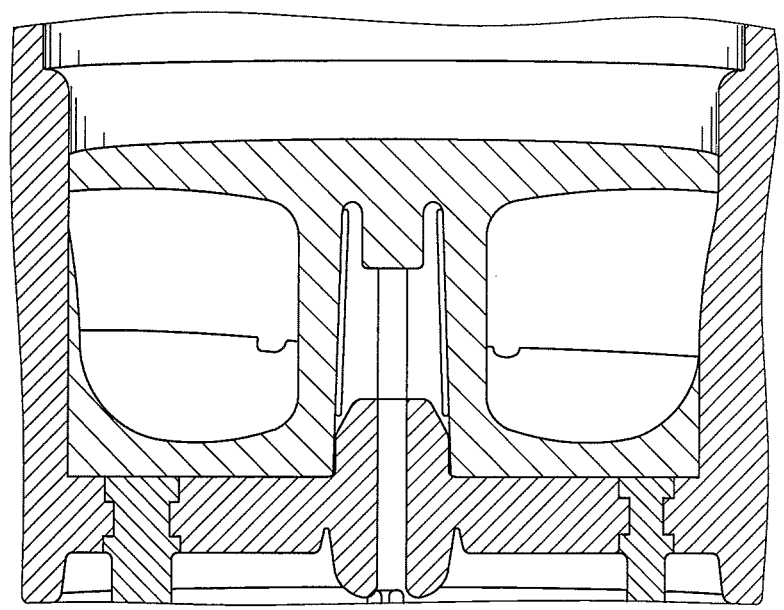
FIG. 4B is a further enlarged side sectional view of the vent tube.
Figure 5:
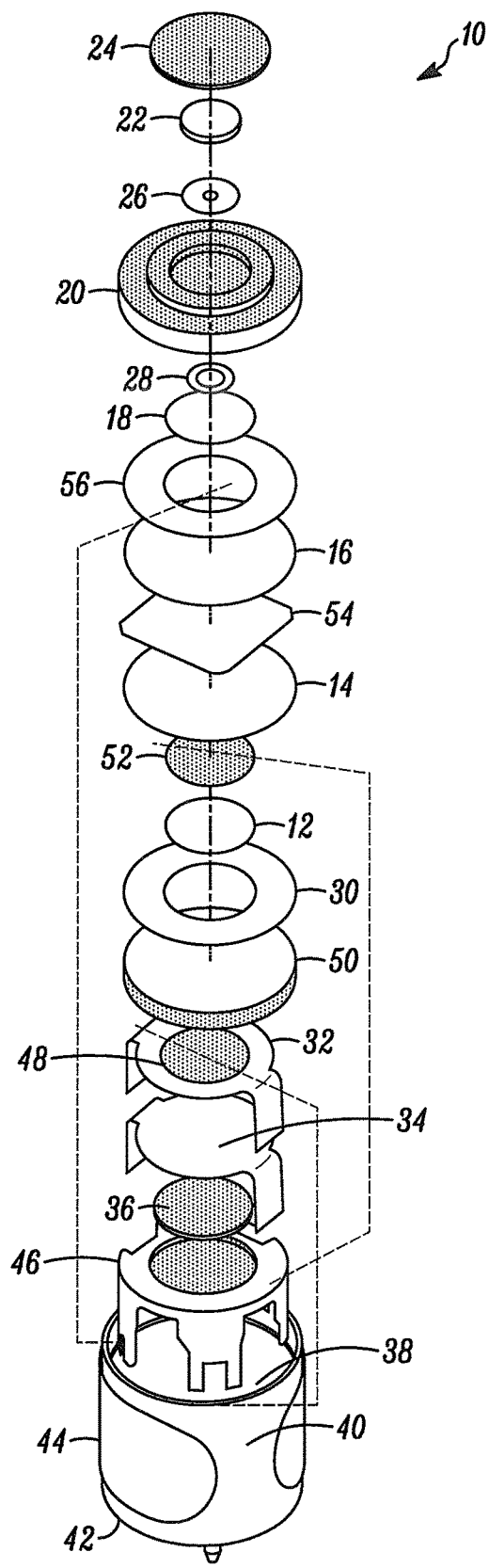
FIG. 5 is an exploded view of another sensor.
Figure 6:
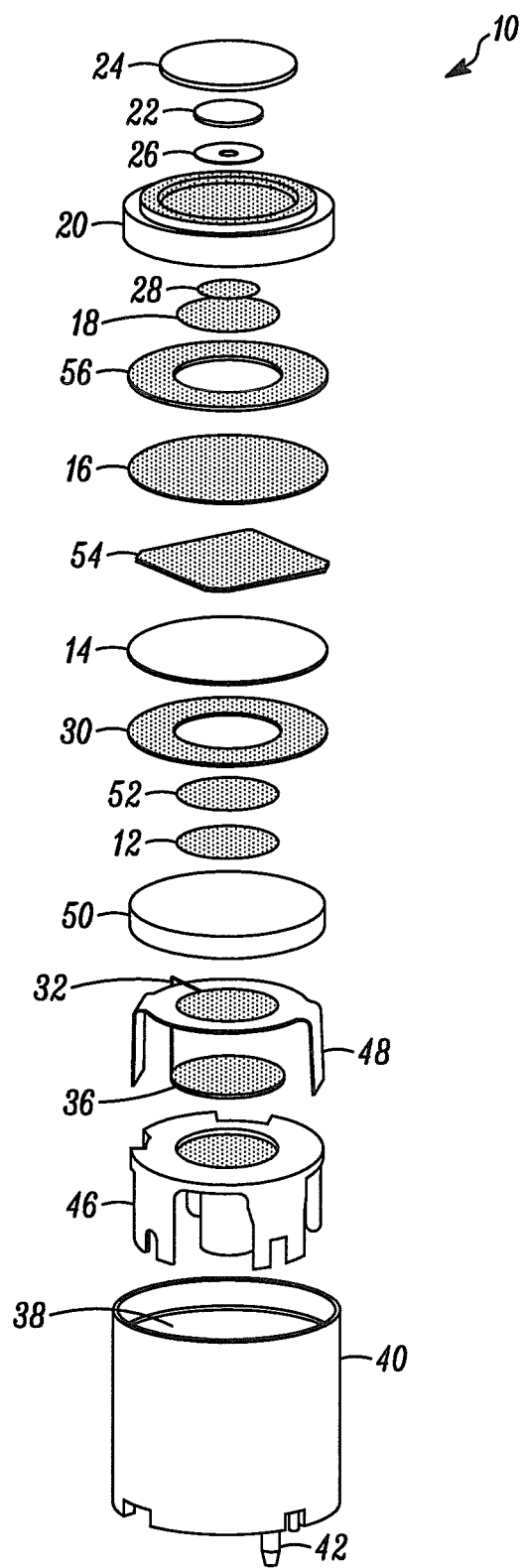
FIG. 6 is an exploded view of another sensor.
Figure 7:
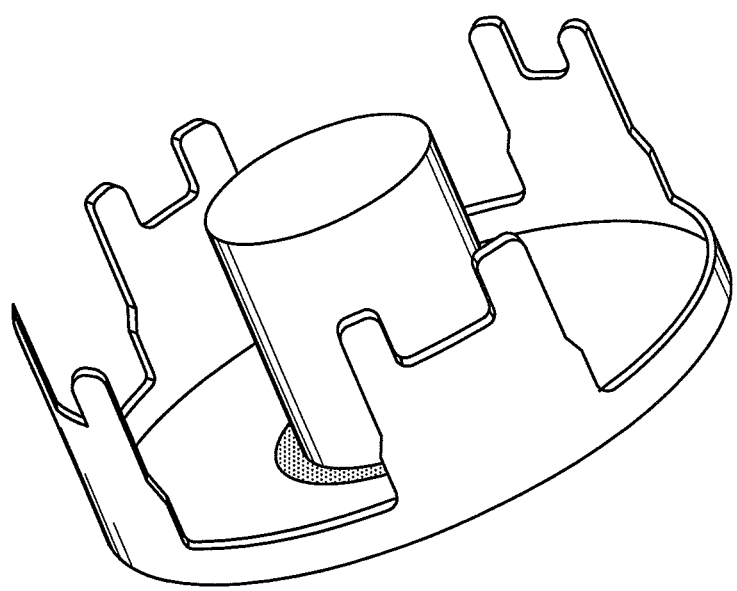
FIG. 7 is an enlarged view of a support table.
Figure 8:
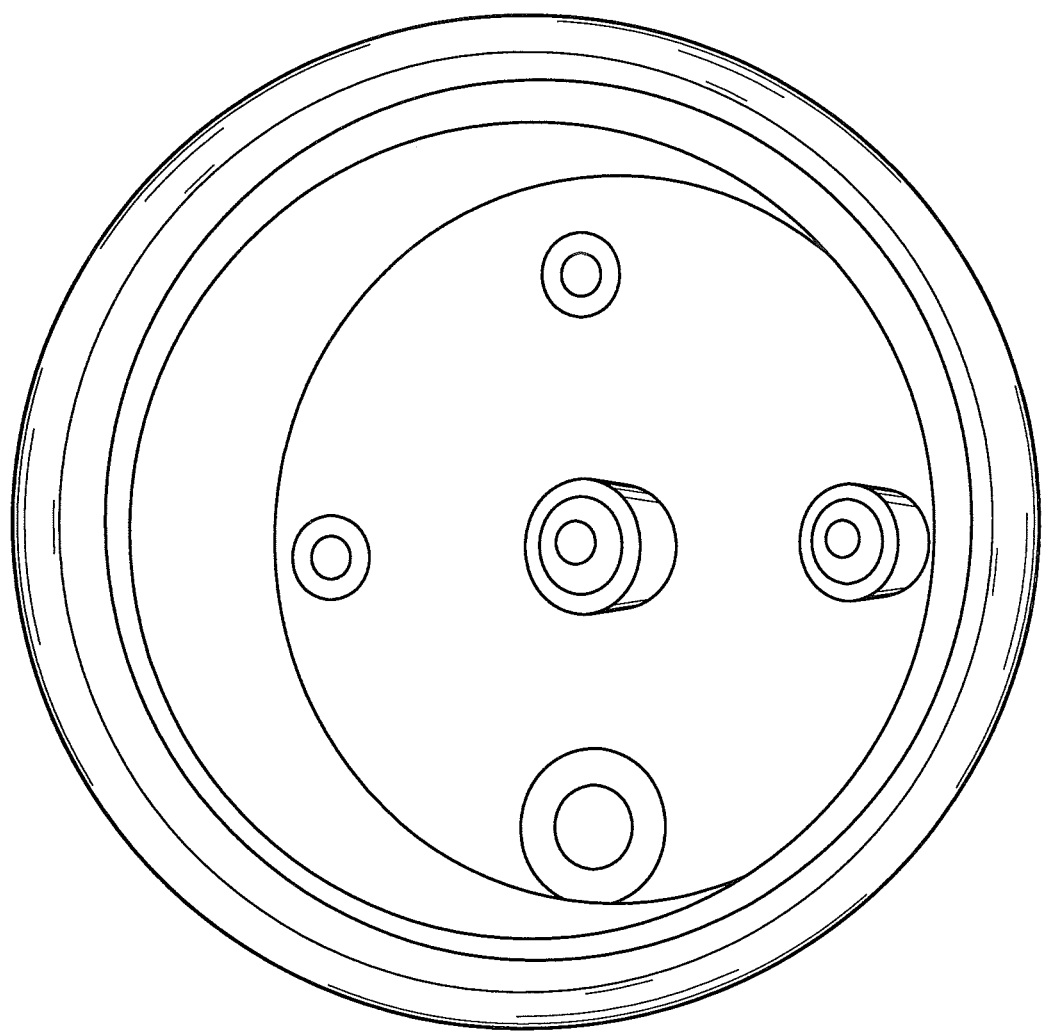
FIG. 8 is an enlarged view of a body.
Figure 9:
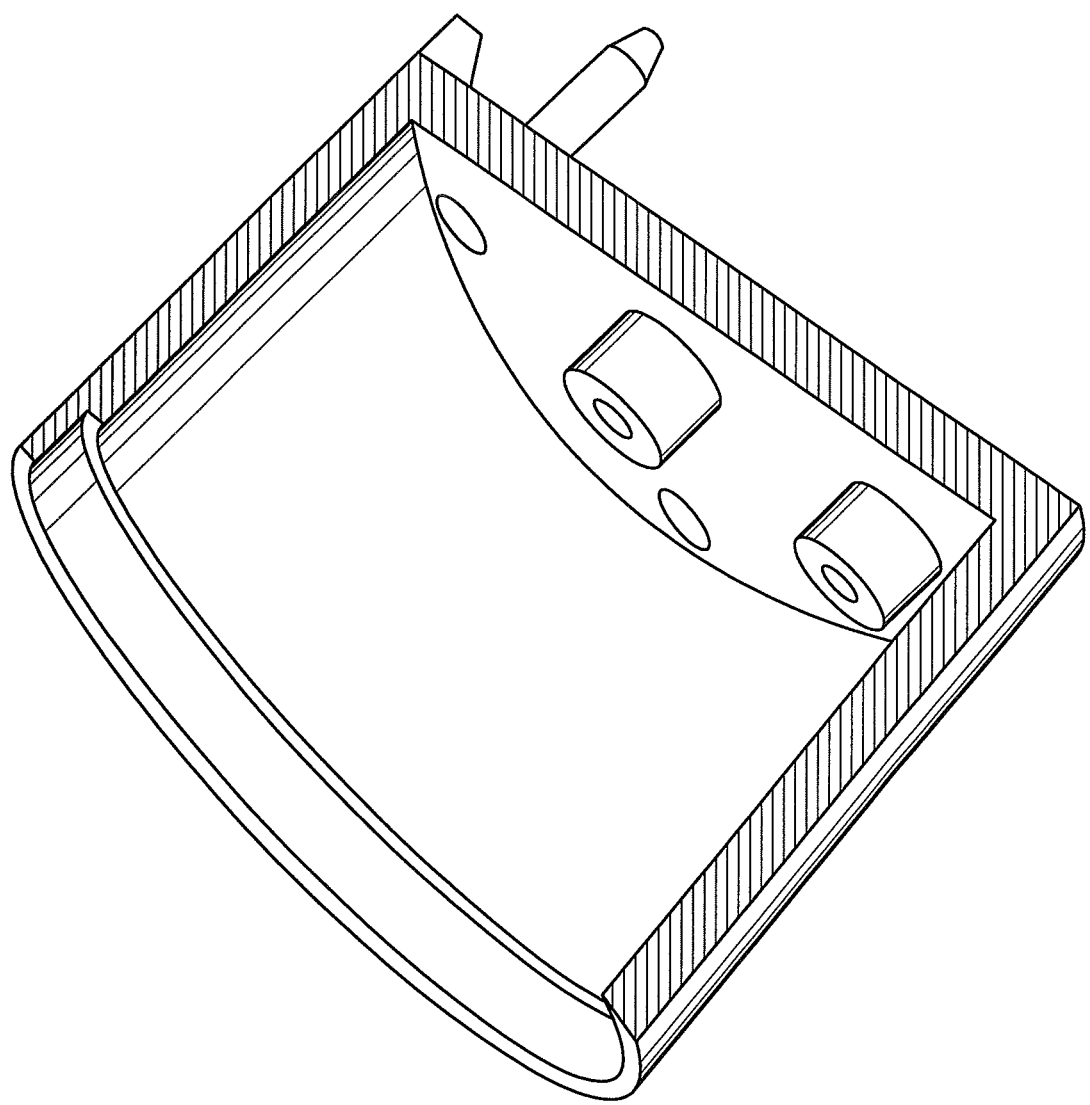
FIG. 9 is an enlarged view of a cross-section of the body.
Figure 10:
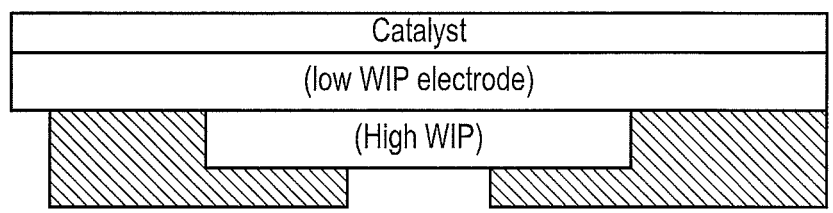
FIG. 10 is an enlarged view of a vent component of a gas sensor.

The Figures illustrate aspects of the embodiments hereof. FIG. 1 illustrates an exploded view of a sensor in accordance herewith. FIGS. 2A, 2B illustrates details of a support table epoxied into a sensor body enclosure. FIG. 3 illustrates a sensor assembly process. FIGS. 4A, 4B illustrate additional aspects of a support table. FIG. 5 illustrates an exploded view of another sensor. FIG. 6 illustrates an exploded view of yet another sensor. FIG. 7 is an enlarged view of a support table. FIG. 8 is an enlarged view of a body. FIG. 9 is an enlarged view of a cross-section of the body. FIG. 10 is an enlarged view of a vent component of a gas sensor.

FIG. 5 refers to the general assembly of one embodiment of an oxygen sensor 10. Starting at the lower end of the sensor 10, there is a body 40, which can be molded from plastic or any inert material. The body 40 has at least one terminal pin 42, which has a platinum current collector (not shown) connected to the top of the terminal pin 42. The at least one current collector runs along the inner wall(s) of the body. In one embodiment, the body has three terminal pins with a corresponding number of current collectors attached to them. The body 40 can optionally have a label on the outer surface. There is an inlet port or hole (not shown) on the body 40 where gas can enter and travel through. The gas inlet port of the body can be a hollow protrusion. The body 40 has a cavity that can contain an electrolyte 38, which can be added via an access hole that is heat-sealed after electrolyte 38 has been added.

Attached to the body 40 is a support table 46 having a gas inlet port in alignment with the gas inlet port of the body, and three legs attached to the perimeter of the body wherein the legs are located near the terminal pins of the body. The gas inlet port of the table can be a central, hollow leg on the same side of the table as the other table legs. The raised protrusion inlet port in the center of the body can snap into the central, hollow leg of the table. In one embodiment, the oxygen sensor 10 has three current collectors and the table 46 has three legs. The perimeter legs of the table have cut-out sections at the bottom of the feet where the current collector(s) can travel under to reach the inner wall(s) of the body. Epoxy (not shown) is dispensed over the tops of the pins 42 causing a seal to be made around the pins 42 so that electrolyte 38 cannot leak around these components. The epoxy also flows into any possible gaps that may be present between the legs of the table 46 and the body 40.

A carbon cloth disk 36 is located on the top surface of the table 46. The carbon cloth disk 36 may be secured to the top surface of the table 46 by adhesive. Optionally, the top of the table 46 may contain a recess for the disk 36 to be seated. On top of the carbon cloth disk 36 is a vent membrane 34, which can be made of polytetrafluoroethylene (PTFE). The vent membrane 34 has at least one tab along the perimeter of the membrane 34, which protrudes from the bottom of the membrane 34. Two tabs are shown but there may be more or less than two. The vent membrane 34 can be heat-sealed over the carbon cloth disk 36 to prevent electrolyte 38 leakage. Placed above the vent membrane 34 is a counter electrode 32, which is seated upon a section of PTFE tape 48. The vent membrane 34 and the section of PTFE tape 48 upon which the counter electrode 32 sits are in intimate contact. Equalization of air pressure within the sensor 10 is achieved by the tabs on both the PTFE tape section and the vent membrane 34. The PTFE tape 48 is gas permeable. A pad 50 is located on top of the counter electrode 32. The pad can be made of glass fiber. The pad 50 can optionally have tabs along its diameter protruding from its bottom surface. A washer separator 30 is located on top of the pad 50. The washer separator 30 can be made of glass fiber.

There is a gas barrier 12 located on top of the washer separator 30 or within the opening of the washer separator 30. The gas barrier 12 can be made of polychlorotrifluoroethylene (PCTFE), as in Aclar® film or Hydroblock® film. Aclar® film can be used as a gas barrier in many gas sensor devices. A reference electrode 52 is located on top of the gas barrier 12. A separator 14 is added on top of the reference electrode 52. A gas barrier 54 is placed on top of the separator 14. The gas barrier 54 can be made of PCTFE, as in Aclar® film or Hydroblock® film. Optionally, the gas barrier 54 can be in the shape of a square to ensure that the separators above it will remain wetted and still be allowed to communicate electrochemically. Above the gas barrier 54 is another separator 16, which can be made of glass fiber. A washer separator 56, which can be made of glass fiber, is situated on top of the separator 16. A sensing electrode 18 is on top of the washer separator 56. A diffuser 28 is located on top of the sensing electrode 18. The diffuser 28 is placed in a recess on the underneath of a cap 20. The sensing electrode is heat-sealed into place on the cap 20, which also serves to prevent electrolyte 38 leakage. After assembly of these components, the cap 20 is placed onto the body 40 and is sealed. The sealing can be accomplished by ultrasonic welding in one embodiment. An adhesive ring 26 is placed on the surface of the cap 20, which surrounds a capillary located in the center of the cap 20. A bulk flow assembly 22 is added on top of the adhesive ring 26. A mesh outer cover 24 can be added to the top of the bulk flow assembly 22. The dashed lines represent current collectors, which run up the inside of the stack of components along the wall of the body 40.

FIG. 6 refers to the general assembly of one embodiment of an oxygen sensor 10. Starting at the lower end of the sensor 10, there is a body 40, which can be molded from plastic or any inert material. The body 40 has at least one terminal pin 42, which has a platinum current collector (not shown) attached to the top of the terminal pin 42. The at least one current collector runs along the inner wall(s) of the body. In one embodiment, the body has three terminal pins with a corresponding number of current collectors attached to them. The body 40 can optionally have a label on the outer surface. There is an inlet port or hole (not shown) on the body 40 where gas can enter and travel through. The gas inlet port of the body can be a hollow protrusion. The body 40 has a cavity that can contain an electrolyte 38, which can be added via an access hole that is heat-sealed after electrolyte 38 has been added.

Attached on the top of the body 40 is a table 46 having a gas inlet port in alignment with the gas inlet port of the body, and at least one leg attached to the perimeter of the body, wherein the leg(s) are located near the terminal pins. The gas inlet port of the table can be a central, hollow leg on the same side of the table as the other leg(s). The raised protrusion inlet port in the center of the body can snap into the central, hollow leg of the table. In one embodiment, the oxygen sensor 10 has three current collectors and the table 46, correspondingly has three legs attached to the perimeter of the body. The perimeter legs of the table have cut-out sections at the bottom of the feet where the current collectors can travel under to reach the inner wall(s) of the body. Epoxy (not shown) is dispensed over the tops of the pins 42 causing a seal to be made around the pins 42 so that electrolyte 38 cannot leak around these components. The epoxy also flows into any possible gaps that may be present between the legs of the table 46 and the body 40.

A carbon cloth disk 36 is located on the top surface of the table 46. The carbon cloth disk 36 may be secured to the top surface of the table 46 by adhesive. Optionally, the top of the table 46 may contain a recess for the disk 36 to be seated. On top of the carbon disk is a counter electrode 32, which is seated upon a section of PTFE tape 48. The tape has at least one tab along the perimeter and protrudes from the bottom. Equalization of air pressure within the sensor 10 is achieved by the tabs on the PTFE tape section 48, which is gas permeable. A pad 50 is located on top of the counter electrode 32. The pad can be made of glass fiber. There is a gas barrier 12 located on top of the pad 50. The gas barrier 12 can be made of polychlorotrifluoroethylene (PCTFE), as in Aclar® film or Hydroblock® film. A reference electrode 52 is located on top of the gas barrier 12. A washer separator 30 is added on top of the reference electrode 52. A separator 14 is placed on top of the washer separator 30. A gas barrier 54 is placed on top of the separator 14. The gas barrier 54 can be made of PCTFE, as in Aclar® film or Hydroblock® film. Optionally, the gas barrier 54 can be in the shape of a square to ensure that the separators above it will remain wetted and still be allowed to communicate electrochemically. Above the gas barrier 54 is another separator 16, which can be made of glass fiber. A washer separator 56, which can be made of glass fiber, is situated on top of the separator 16. A sensing electrode 18 is on top of the washer separator 56. A diffuser 28 is located on top of the sensing electrode 18. The diffuser 28 is placed in a recess on the underneath of a cap 20. The sensing electrode is heat-sealed into place on the cap 20, which also serves to prevent electrolyte 38 leakage. After assembly of these components, the cap 20 is placed onto the body 40 and is sealed. The sealing can be accomplished by ultrasonic welding in one embodiment. An adhesive ring 26 is placed on the surface of the cap 20, which surrounds a capillary located in the center of the cap 20. A bulk flow assembly 22 is added on top of the adhesive ring 26. A mesh outer cover 24 can be added to the top of the bulk flow assembly 22. The dashed lines in the Figure represent current collectors (not shown), which run up the inside of the stack of components along the wall of the body 40.

It is known that electrochemical gas sensors contain a significant volume of internal "free space" within the housing that is filled with air throughout the majority of the operational lifetime of the sensor. As the sensor housing is typically sealed to prevent release of electrolyte, air remains trapped within the sensor and that air can be affected by changes in local environmental conditions (specifically temperature and pressure) as described by the "gas laws". Pressure differentials between the atmosphere in the sensor and that outside the sensor can disrupt the performance of the device. The present gas sensor provides a route that links the internal and external atmospheres, as exemplified here by the path from the electrode stack through the table support to the external vent. This path provides sufficiently low flow resistance to ensure that pressure equalizes quickly under all operating conditions. Moreover, all spaces within the sensor requiring venting are intimately linked, noting that their position can be affected by sensor orientation and external forces such as vibration and shock. This can be problematic when inert, porous polymers (e.g. polypropylene or PTFE) are used as vents since sealing by means of thermal welding or compression (e.g. using 'O' rings) can critically restrict the material porosity. The present gas sensor incorporates a porous vent component and seals it to the enclosure without the sealing mechanism critically affecting the vent functionality.

The vent component (FIG. 10) of the present gas sensor employs two PTFE tapes with different material properties to separate the differing aspects of the functionality. High water ingress pressure (WIP) PTFE can affect a robust seal and the low WIP PTFE can affect a robust lateral vent that can access many pockets of gas within the sensor enclosure, using a "tabbed/winged" component geometry as shown, in the section of PTFE tape 48, in FIG. 6. A disc of high WIP PTFE tape is heat sealed over a vent hole and allows sufficient air to flow through (perpendicular to the sheet plane) it to prevent undesirably high pressure differentials between the internal and external environments. A low WIP, high porosity PTFE tape is then laid across and held in intimate contact with the disc of high WIP PTFE tape so that lateral (in sheet plane) diffusion rate of air flow within the low WIP, high porosity PTFE is sufficiently high to effectively vent air between the internal and external environments. Low WIP, high porosity PTFE is also compatible with electrode deposition onto its surface.

A strong, high WIP porous PTFE tape, grade 6 natural, manufactured by GORE® or Mupor high WIP can be used to provide the seal. The venting capability of this material has previously been demonstrated and importantly it forms a robust seal to the Noryl® engineering plastic used in the housing and is strong enough to be handled in production processes. Mupor PTFE tape, Grade PM17Y, can be used as the counter electrode tape.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A sensor comprising:
    a body comprising at least one terminal pin connected to at least one current collector and a gas inlet port;
    a table with a gas inlet port in alignment with the gas inlet port of the body and at least one leg seated on the body near the at least one terminal pin;
    a vent membrane carried on the table;
    a carbon cloth between the table and the vent membrane;
    a counter electrode carried on the vent membrane;
    a reference electrode in communication with but separated from the counter electrode by at least one washer or pad;
    a sensing electrode in communication with but separated from the reference electrode by at least one washer or pad; and
    a cap on top of the sensing electrode, in which cap attaches to the body
    and forms a seal to contain an enclosed electrolyte.

2. The sensor of claim 1, wherein the vent membrane comprises polytetrafluoroethylene.

3. The sensor of claim 1, wherein the counter electrode is seated upon a section of polytetrafluoroethylene tape.

4. The sensor of claim 1, further comprising a washer separator on top of the pad between the counter electrode and the reference electrode.

5. The sensor of claim 4, further comprising a gas barrier on top of the washer separator between the counter electrode and the reference electrode.

6. The sensor of claim 5, wherein the gas barrier comprises polychlorotrifluoroethylene.

7. The sensor of claim 1, further comprising a separator between the reference electrode and the sensing electrode wherein the separator lies on top of the reference electrode.

8. The sensor of claim 1, further comprising a gas barrier between the reference electrode and the sensing electrode wherein the gas barrier lies on top of a separator.

9. The sensor of claim 1, further comprising a separator between the reference electrode and the sensing electrode wherein the separator lies on top of a gas barrier.

10. The sensor of claim 1, further comprising a washer separator between the reference electrode and the sensing electrode wherein the washer separator lies on top of a separator.

11. The sensor of claim 1, further comprising a diffuser on top of the sensing electrode.

12. The sensor of claim 1, further comprising a separator between the reference electrode and the sensing electrode wherein the separator lies on top of a gas barrier and below the cap.

13. The sensor of claim 1, further comprising an adhesive ring on the surface of the cap.

14. The sensor of claim 1, further comprising a bulk flow assembly, which lies on top of an adhesive ring.

15. The sensor of claim 1, further comprising a mesh outer cover, which lies on top of a bulk flow assembly.

16. The sensor of claim 1, wherein epoxy is used as a sealant.

17. The sensor of claim 1, wherein the at least one current collector is located along an inner wall of the body.

18. A sensor comprising:
a body;
an electrode stack comprising a sensing electrode and a counter electrode;
an electrolyte;
at least one separator positioned between the sensing electrode and the counter electrode,
a gas barrier disposed in contact with at least one separator between the counter electrode and the reference electrode, wherein the gas barrier comprises polychlorotrifluoroethylene;
a table with at least one leg seated on the body;
a vent membrane carried on the table;
a carbon cloth between the table and the vent membrane, wherein the electrode stack is positioned on the vent membrane.

19. A sensor comprising:
a body having an internal cavity and a first gas inlet port comprising a protrusion in the center of the body;
an electrode stack disposed within the internal cavity, wherein the electrode stack comprises at least a sensing electrode and a counter electrode;
electrolyte carried within the internal cavity between the electrodes;
a table attached inside of the internal cavity which carries the electrode stack, wherein the table comprises a hollow central leg and a second gas inlet port in alignment with the first gas inlet port of the body, wherein the hollow central leg sits over the protrusion of the first gas inlet portion of the body;
wherein the table provides a venting route connecting a selected region of the electrode stack to an outside surface of the housing;
a vent membrane carried on the table;
a carbon cloth between the table and the vent membrane.

20. A sensor comprising:
a housing,
at least two electrodes,
an electrolyte, and
a vent membrane in communication with a vent leading to an external atmosphere, wherein the vent membrane comprises a first polytetrafluoroethylene (PTFE) material and a second PTFE material, wherein the first PTFE material is sealed over the vent, and wherein the second PTFE material is held in contact with the first PTFE between the first PTFE material and the at least two electrodes and the electrolyte, wherein the first PTFE material has a higher water ingress pressure (WIP) than the second PTFE material.

21. The sensor of claim 20, further comprising a table attached inside of the housing, wherein the table is configured to support the at least two electrodes and comprises the vent, and wherein the second PTFE material comprises one or more tabs that extend over the tab and along one or more sides of the table.

* * * * *